United States Patent [19]

Umezawa et al.

[11] 4,164,567
[45] Aug. 14, 1979

[54] PROCESS FOR RECOVERING MACROMOMYCIN

[75] Inventors: Hamao Umezawa; Tomio Takeuchi, both of Tokyo, Japan

[73] Assignee: Zaidan Hojin Biseibutsu Kagaku Kenkyu Kai, Tokyo, Japan

[21] Appl. No.: 801,492

[22] Filed: May 31, 1977

[51] Int. Cl.² ............................................. A61K 35/00
[52] U.S. Cl. .................................................... 424/123
[58] Field of Search ........................................ 424/123

[56] References Cited
U.S. PATENT DOCUMENTS 3,505,449  4/1970  Harned ................................. 424/123
3,595,954  7/1971  Umezawa et al. .................... 424/117

*Primary Examiner*—Jerome D. Goldberg
*Attorney, Agent, or Firm*—Herbert W. Taylor, Jr.

[57] ABSTRACT

There is provided a process for recovering macromomycin (hereinafter referred to as MCR) which comprises adding coagulants or coagulants and neutralizers to a culture filtrate saturated with ammonium sulfate and collecting the resulting precipitate containing MCR in a high yield at low centrifugal force. From the precipitate obtained, MCR powders can be prepared according to the methods described in U.S. Pat. No. 3,595,954 and others.

3 Claims, No Drawings

PROCESS FOR RECOVERING MACROMOMYCIN

BACKGROUND OF THE INVENTION

1. Field of the Invention

The present invention provides a process for the recovery of a precipitate containing the antitumor antibiotic macromomycin (MCR) for a culture filtrate in a high yield.

2. Description of the Prior Art

MCR was found in a culture filtrate of *Stremptomyces macromomyceticus* as an antitimor antibiotic exhibiting strong inhibition of the tumor growth, as shown in U.S. Pat. No. 3,595,954.

Hitherto, when MCR is to be recovered from a culture filtrate by salting-out, the culture filtrate has been saturated with ammonium sulfate and allowed to stand at a low temperature for several hours, and then the precipitate obtained has been collected by centrifugation. However, in this case, the precipitate sedimented with difficulty and centrifugal force of at least 25,000×G for 10 minutes was required in order to recover at least 60% of MCR from the culture filtrate. The application of this process to industrial production is virtually impossible because the industrial centrifuge bearing such a high centrifugal force does not exist.

SUMMARY OF THE INVENTION

The present invention relates to a process for forming and recovering a precipitate containing MCR.

The present inventors have searched for a coagulant for facilitating the recovery of the precipitate containing MCR preferably by centrifugation and, as shown in Table 1, it was found that MCR salted-out was coprecipitated forming large flocks with other materials by the addition of compounds exhibiting a coagulating effect such as ferrous sulfate, ferrous chloride, ferric sulfate, ferric chloride, sodium aluminate and aluminum sulfate and this precipitate containing MCR could be collected even by centrifugal force of 1000×G for 10 minutes.

The effective concentrations of the iron salts, i.e. ferrous sulfate, ferrous chloride, ferric sulfate and ferric chloride, are at least 0.1 percent but the suitable amount is at least 0.5 percent by weight of the volume of the culture filtrate.

The effective concentrations of aluminum sulfate, sodium aluminate and polyaluminum chloride are at least 0.05 percent, preferably from about 0.1 to about 0.3 percent by weight of the volume of the culture filtrate.

High molecular coagulants such as sodium alginate, carboxymethylcellulose (CMC) sodium salt, sodium polyacrylate, polyaluminum chloride and others are also useful.

When the pH of the solution changes substantially upon adding a coagulant, a neutralizer should be added before the coagulant. As shown in Table 2 it was found that when the pH of the solution was kept neutral so that MCR was stable then the recovery of MCR was remarkably improved by adding a neutralizer selected from the group consisting of sodium carbonate, calcium carbonate, sodium bicarbonate, dibasic sodium phosphate, dibasic potassium phosphate, monobasic sodium phosphate, monobasic potassium phosphate and others, prior to the addition of a coagulant, to a culture filtrate saturated with ammonium sulfate. Ferric chloride and aluminum sulfate are excellent among the coagulants and in these cases sodium carbonate and calcium carbonate are suitable as a neutralizer.

Ferric chloride in an amount of at least 0.1 percent by weight of the volume of the culture filtrate and sodium carbonate or calcium carbonate in an amount of at least 0.1 percent by weight of the volume of the culture filtrate are sufficiently effective. However, the concentrations of ferric chloride and sodium carbonate or calcium carbonate are both preferably from about 0.2 percent to about 0.5 percent by weight of the volume of the culture filtrate, thus at least 70 percent of MCR in a culture filtrate can be recovered in the precipitate obtained.

It is preferable to adjust pH of the solution to 5.0–7.5 by the addition of the coagulant and the neutralizer for the effective performance of the present invention.

The coagulant and the neutralizer are added preferably in forms of aqueous solutions thereof.

The neutralizer and the coagulant may be added prior to the saturation with ammonium sulfate. The saturation with ammonium sulfate is preferably at least 60 percent, more preferably at least 90 percent.

As explained above, the present invention makes it possible for MCR to be readily recovered as a precipitate containing MCR from a culture filtrate on an industrial scale.

TABLE 1

The Effect of Adding Coagulants on Ammonium-sulfate Salting-out of MCR

| Coagulant | Concentration in percent by weight | pH | Recovery of MCR |
|---|---|---|---|
| control | 0% | 6.7 | 0% |
| Ferrous chloride | 0.5 | 6.3 | 9 |
| Ferrous sulfate . 7 $H_2O$ | 0.5 | 6.4 | 20 |
| Ferric chloride . 6 $H_2O$ | 0.5 | 2.8 | 28 |
| Ferric sulfate | 0.5 | 3.7 | 10 |
| Sodium aluminate | 0.1 | 7.2 | 37 |
| Aluminum sulfate | 0.25 | 2.9 | 19 |

(a) A culture filtrate containing MCR was 100% saturated with ammonium sulfate and allowed to stand at 5° C. for 5 hours. To this solution was added an aqueous solution of a coagulant. After one hour, the resulting precipitate was collected by centrifugation at 1,000×G for 10 minutes. This precipitate was dissolved with 0.1 M citric acid phosphate buffer (pH 7.0) and the activity of MCR was measured. The recovery of MCR was calculated from the ratio of the activity of the precipitate to that of the culture filtrate used.

(b) The activity of MCR was measured by the following microbial assay method.

MCR powders were dissolved in 0.1 M citric acid phosphate buffer (pH 7.0), thus solutions containing 500 mcg. and 125 mcg. of MCR per ml. were prepared as standard solutions of MCR. The method of determining the activity described in U.S. Pat. No. 3,595,954 according to the cylinder agar plate method was used. *Micrococcus flavus* FDA16 was used as the test organism.

TABLE 2

Combined Effect of a Coagulant and a Neutralizer on Ammonium-sulfate Salting-out of MCR

| Coagulant in percent by weight | | Neutralizer in percent by wt. | | pH | Recovery of MCR |
|---|---|---|---|---|---|
| (Control) | 0% | — | 0% | 6.1 | 0 |
| Aluminum Sulfate | 0.2 | Calcium carbonate | 1.0 | 7.1 | 44 |

TABLE 2-continued

Combined Effect of a Coagulant and a Neutralizer on Ammonium-sulfate Salting-out of MCR

| Coagulant in percent by weight | | Neutralizer in percent by wt. | | pH | Recovery of MCR |
|---|---|---|---|---|---|
| " | 0.5 | " | 2.0 | 7.0 | 49 |
| Ferric chloride . $6H_2O$ | 0.1 | " | 0.1 | 7.2 | 52 |
| " | 0.25 | " | 0.25 | 7.2 | 74 |
| " | 0.5 | " | 0.5 | 7.3 | 76 |
| " | 1.0 | " | 1.0 | 7.2 | 71 |
| " | 0.1 | Sodium carbonate | 0.1 | 7.2 | 60 |
| " | 0.25 | " | 0.25 | 7.1 | 75 |
| " | 0.5 | " | 0.5 | 7.1 | 75 |
| " | 1.0 | " | 1.0 | 7.1 | 74 |

(a) A culture filtrate containing MCR was 100% saturated with ammonium sulfate and allowed to stand at 5° C. for 5 hours. Then, to this solution, an aqueous solution of a neutralizer was added, whereupon, immediately, an aqueous solution of a coagulant was admixed.

Subsequent procedures and the measuring method of the MCR activity are described in (a) and (b) of Table 1.

The following examples are illustrative of the present invention and are not intended to limit the scope thereof.

DESCRIPTION OF THE PREFERRED EMBODIMENTS

EXAMPLE 1

Rapid centrifugation of 6 l fermentation broth containing MCR yielded 5 l of a supernatant liquid. The supernatant liquid thus obtained was adjusted to pH 7.0 and cooled to 5° C. To 5 l of this solution, 3.5 kg of ammonium sulfate was added and stirred until in solution. Then the solution was allowed to stand at 5° C. with intermittent stirring for 5 hours. To the solution saturated with ammonium sulfate, an aqueous solution of 25 g of sodium carbonate was added, whereupon, immediately, an aqueous solution of 25 g of ferric chloride.$6H_2O$ was added. pH of this solution was 7.2. After stirring for one hour, a precipitate containing MCR was collected by centrifugation at 2000×G for 10 minutes in the cold. The yield of the MCR activity of the precipitate was 72 percent.

The precipitate was dissolved with deionized water and insoluble materials were removed by centrifugation. The solution thus obtained was placed in a cellophane tube and dialyzed against tap water for 24 hours. The inner solution containing MCR was applied to a column filled with chlorinated type of Amberlite IRA-410. to 1 l of this effluent, 700 g of ammonium sulfate was added, dissolved and allowed to stand at 5° C. for 24 hours. Then, an aqueous solution of 5 g of sodium carbonate was added, whereupon, immediately, an aqueous solution of 5 g of ferric chloride.$6H_2O$ was admixed. The precipitate was collected by centrifugation at 2000×G for 10 minutes and dissolved with deionized water. Insoluble materials were removed by centrifugation. The supernatant liquid obtained was dialyzed in a cellophane tube. This inner solution was applied to a column filled with Sephadex G-25 and chromatographed with deionized water. The active fractions containing MCR were collected and lyophilized. Crude powders of MCR thus obtained (310 mg) were dissolved in 50 ml of deionized water. This solution was applied to a column filled with Sephadex G-50, chromatographed with deionized water. The active fractions were collected and lyophilized. MCR powders (110 mg) were obtained. The activity of MCR was measured according to the method described in Table 1, i.e. the cylinder agar plate method using *Micrococcus flavus* as the test organism.

EXAMPLE 2

One liter of fermentation broth containing MCR was centrifuged for removing cells to yield 800 ml of a supernatant liquid, pH of which was 7.1. To 800 ml of the supernatant liquid, 560 g of ammonium sulfate was added, stirred until in solution. Then, the solution was allowed to stand at 5° C. for 16 hours, whereupon an aqueous solution of 0.8 g of sodium aluminate was admixed. pH of the resulted solution was 7.4. The precipitate was collected by centrifugation at 2000×G for 10 minutes. The recovery of the MCR activity in the precipitate was 32 percent. The measurement of the MCR activity was made in accordance with the method described in Table 1.

While the described embodiments represents the preferred forms of the present invention, it is to be understood that modifications will occur to those skilled in the art without departing from the spirit of the invention.

We claim:

1. A process for forming a precipitate containing macromomycin from a macromomycin culture which comprises, adding a neutralizer to a culture filtrate of macromomycin in a saturated solution of ammonium sulfate which is maintained at a temperature of about 5° C., said neutralizer (a) being added in an amount in the range of from 0.25 percent to 1.0 percent based on the weight of said macromomycin culture and (b) being selected from the group consisting of sodium carbonate, calcium carbonate, sodium bicarbonate, dibasic sodium phosphate, dibasic potassium phosphate, monobasic sodium phosphate and monobasic potassium phosphate, immediately thereafter, adding a coagulant to said macromomycin culture that is neutralized by said neutralizer, said coagulant, (a) being added in an amount of from 0.25 percent to 1.0 percent, based on the weight of said macromomycin culture, to provide a mixture having a pH in the range of 5.0 to 7.5, and (b) being selected from a group consisting of ferrous sulfate, ferrous chloride, ferric sulfate, ferric chloride, sodium aluminate, aluminum sulfate, and recovering a precipitate containing a high concentration of macromomycin therefrom.

2. The process of claim 1 wherein said neutralizer is an aqueous solution of calcium carbonate and said coagulant is an aqueous solution of ferric chloride.

3. The process of claim 1 wherein said neutralizer is an aqueous solution of sodium carbonate and said coagulant is an aqueous solution of ferric chloride.

* * * * *